Figure 1:
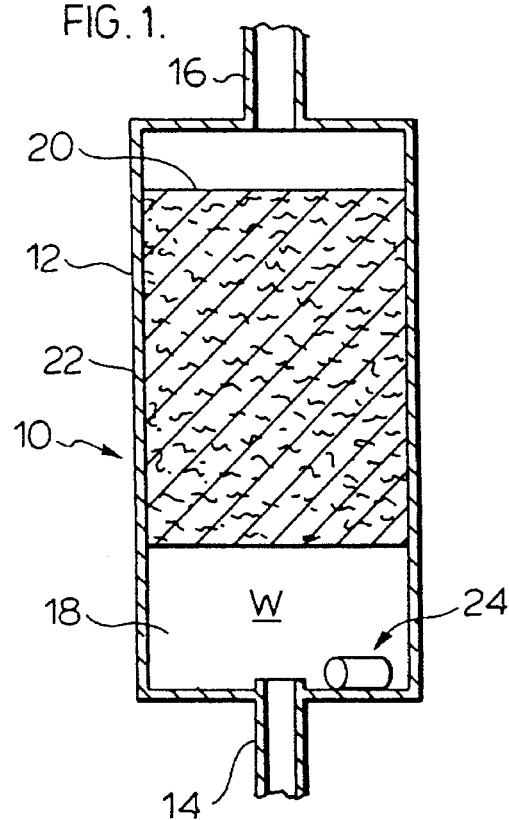

United States Patent [19]

Butler

[11] Patent Number: 5,525,223
[45] Date of Patent: Jun. 11, 1996

[54] APPARATUS FOR INTRODUCING AN AGENT INTO A LIQUID OR GAS AT A CONTROLLED RATE

[76] Inventor: Ernest Butler, 1083 First Avenue, N.W., Moose Jaw, Saskatchewan, Canada, S6H 3N1

[21] Appl. No.: 961,633

[22] Filed: Oct. 16, 1992

[51] Int. Cl.⁶ .................................................. C02F 9/00
[52] U.S. Cl. ........................ 210/202; 210/266; 210/284
[58] Field of Search .................................... 210/198.1, 202, 210/205, 206, 753, 282, 201, 203, 259, 266, 284; 222/1, 54, 190; 422/277; 55/261, 262

[56] References Cited

U.S. PATENT DOCUMENTS

| | | | |
|---|---|---|---|
| 3,414,515 | 12/1968 | Mehltretter et al. | 210/917 |
| 4,152,262 | 5/1979 | Rose | 210/206 |
| 4,208,747 | 6/1980 | Dirksing | 4/228 |
| 4,217,331 | 8/1980 | Schaub | 422/277 |
| 4,350,666 | 9/1982 | Klutts | 422/277 |
| 4,382,862 | 5/1983 | Dillman | 210/282 |
| 4,781,805 | 11/1988 | Dahlgren | 204/152 |
| 5,211,973 | 5/1993 | Nohren | 210/282 |

*Primary Examiner*—Ivars Cintins

[57] ABSTRACT

The present invention provides an agent dispenser, a method and an apparatus for introducing an agent into a liquid or gas where the agent is miscible with such liquid or gas. The agent dispenser comprises a hollow casing constructed of a material having a coefficient of cubical expansion that differs from the coefficient of cubical expansion of the liquid or gas. At least one opening is provided in the hollow casing for permitting the flow of the liquid or gas to and from the interior of the hollow casing. The dispenser contains the agent and the agent is introduced into the liquid or gas through liquid or gas drawn into and expelled from said dispenser as a result of variations in the internal pressure of the dispenser resulting from thermal expansion and contraction of the dispenser and its contents caused by variations in the temperature of the liquid or gas surrounding the dispenser.

4 Claims, 4 Drawing Sheets

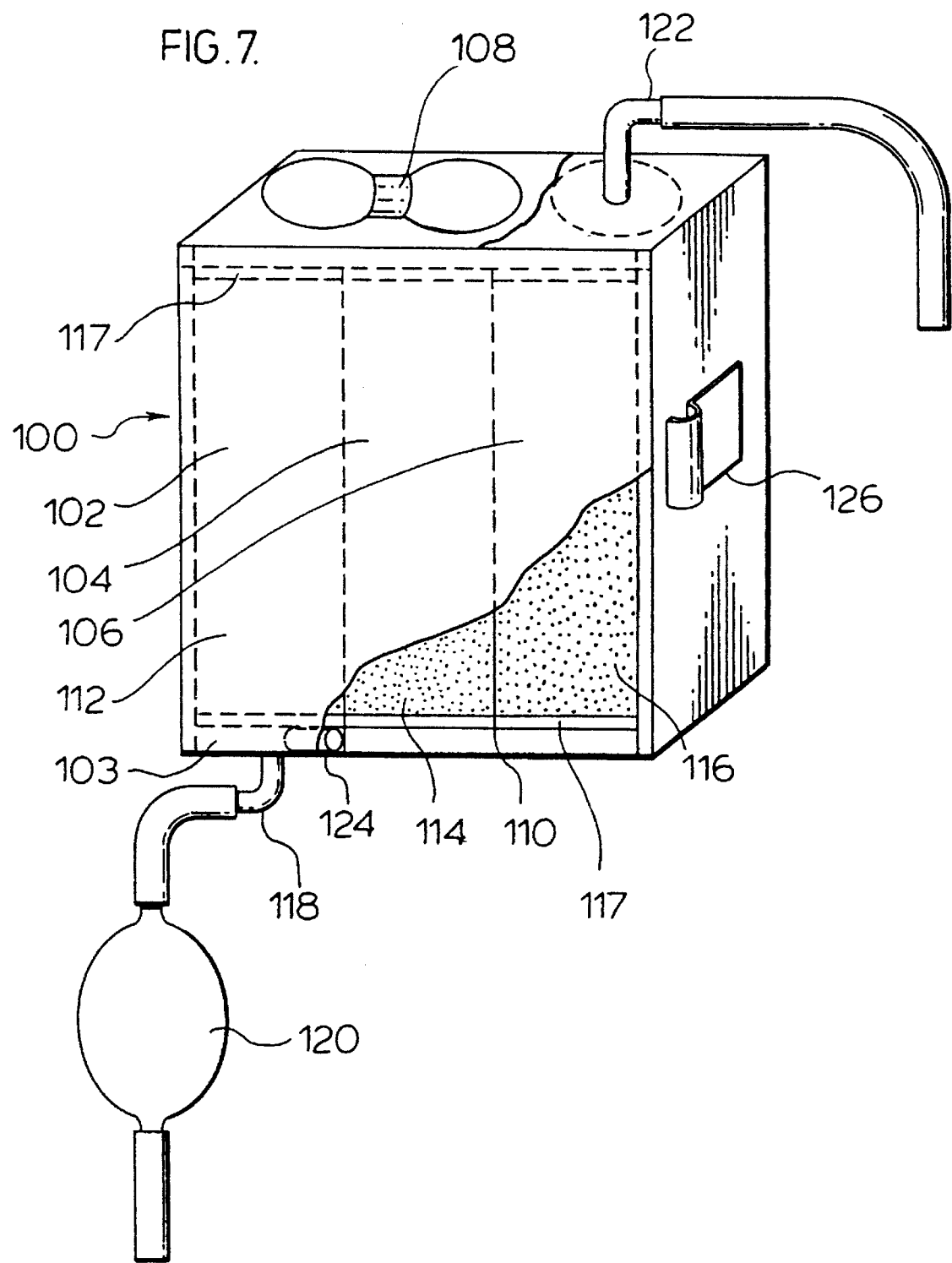

APPARATUS FOR INTRODUCING AN AGENT INTO A LIQUID OR GAS AT A CONTROLLED RATE

FIELD OF THE INVENTION

The present invention relates to an agent dispenser, a method and an apparatus for introducing an agent into a liquid or gas at a controlled rate, and more particularly to an agent dispenser, a method and an apparatus that relies upon temperature fluctuations in the liquid or gas to control the rate of introduction of the agent into the liquid or gas.

BACKGROUND OF THE INVENTION

Means for introducing agents into a surrounding liquid or gas are known. For instance, spray canisters connected to electric timers may be used to eject a scented gas or insect repellant into the air of a room at regular intervals. Also, perforated containers filled with chlorine crystals or tablets may be placed in the water of swimming pools to allow chlorine to seep into the surrounding water by the action of water passing through the perforated container.

In instances where it is desirable to introduce an agent into a gas or liquid, it is often also desirable to control the amount of agent being introduced. However in systems where the gas or liquid is flowing at random intervals, it can be especially difficult to control the degree to which an agent is introduced into the system. In such cases, it is desirable to have a system capable of responding to the random flow of the gas or liquid.

Systems which react directly to the random flow of a liquid or gas are known. A common example of such a system is the disinfectant dispenser sometimes used in household toilet tanks. This system incorporates a float valve which reacts to changes in the water level of the tank and dispenses a dose of disinfectant accordingly. A more sophisticated system is the Apparatus for Purifying Water described by Polley in U.S. Pat. No. 4,059,522. This system incorporates a Venturi tube in a primary water flow path to create a pressure differential and force a small portion of the water through a by-pass leading to an iodine saturation container. Once permitted to be saturated with iodine, the water is returned to the primary water line to purify the water supply.

Both systems described above use the pressure of randomly flowing water to control the introduction of agents into the water supply. The present invention is designed to provide a system that responds to changes in temperature in the random flow of a liquid or gas to control the introduction of agents into the liquid or gas supply.

One particular use for such a system lies in the field of water treatment. One of the problems associated with the treatment of domestic or institutional water systems is the relatively intermittent nature of the flow of water in such systems and the resultant bacterial buildup that can occur. In domestic or institutional water systems, bodies of water are stored in containers or tanks where the water may be drawn off from time to time. Makeup water is added to the container or tank when an equal amount of water is drawn off. Often the water that is drawn off must first pass through a filter element. Typically such filter elements are immersed in the container or tank itself. The containers or tanks are normally located in the interior of a building where the temperature will normally be at room temperature in the region of 20° to 22° C. At these temperatures, and with the water essentially motionless for varying lengths of time, bacteria within the water tend to settle on the filter and grow relatively actively. This can lead to rapid contamination of the filter and create health risks.

The present invention can be used in this circumstance to provide a system to treat the water standing in the container or tank with iodine following each time a fresh flow of water enters the system. When the iodine-treated water passes through the filter, the iodine remains on the filter and kills any bacteria that may exist.

SUMMARY OF THE INVENTION

The present invention provides an agent dispenser for use in introducing an agent into a liquid or gas where the agent is miscible with such liquid or gas. The agent dispenser comprises a hollow casing constructed of a material having a coefficient of cubical expansion that differs from the coefficient of cubical expansion of the liquid or gas. At least one opening is provided in the hollow casing for permitting the flow of the liquid or gas to and from the interior of the hollow casing. The dispenser contains the agent and the agent is introduced into the liquid or gas through liquid or gas drawn into and expelled from said dispenser as a result of variations in the internal pressure of the dispenser resulting from thermal expansion and contraction of the dispenser and its contents caused by variations in the temperature of the liquid or gas surrounding the dispenser.

The present invention further provides a method for introducing an agent into a liquid or gas supply at a controlled rate, where the agent is miscible with such liquid or gas. The method comprises the following steps: (a) placing at least one agent dispenser, described above, into a reservoir, (b) introducing the liquid or gas into the reservoir, and (c) intermittently discharging the liquid or gas from the reservoir and reintroducing new liquid or gas to the reservoir. As described above, the agent is introduced into the liquid or gas in the reservoir through the entry and expulsion of liquid or gas into and from the dispenser, which is driven by variations in the internal pressure of the dispenser resulting from thermal expansion and contraction of the dispenser and its contents due to variations in temperature of the liquid or gas in the reservoir.

The present invention further provides an apparatus for introducing an agent into a liquid or gas at controlled rate, where the agent is miscible with such liquid or gas. The apparatus comprises a reservoir for storing the liquid or gas, inlet means for supplying the liquid or gas to the reservoir, outlet means for discharging the liquid or gas from the reservoir, and at least one agent dispenser described above located in the reservoir.

In one application for the invention, the avoidance of contamination of water filters, one aspect of the invention provides a method and apparatus for introducing iodine into water at a controlled rate. When the iodine-treated water passes through the filter, the iodine remains on the filter and kills any bacteria that may exist. The thermal expansion of the dispenser and its contents is due to changes in temperature caused by flow of the main supply of water.

When the water is not flowing, the temperature of the water contained within the dispenser is generally equal to the temperature of the surrounding water in the reservoir, both being at a resting or room temperature. The water resident within the dispenser will become saturated with the agent.

When water is drawn from the reservoir, the primary supply of water begins to flow to the reservoir. The invention contemplates a temperature differential between incoming water and water remaining in the reservoir. In a preferred embodiment, the incoming water would be significantly warmer or cooler than the normal resting or room temperature of water in the reservoir. As the temperature of the surrounding water within the reservoir changes due to the warmer or cooler incoming supply, the volume of the water and the volume of the dispenser will also change following the laws of thermodynamics.

If the incoming supply of water is cooler, the dispenser and its contents will gradually cool, and the volume of the water within the dispenser will gradually decrease as will the volume of the dispenser. Since the dispenser is constructed of a material having a coefficient of cubical expansion larger or smaller than the coefficient of cubical expansion of the liquid or gas, the rate of contraction of each will differ. In the case of a crystalline polystyrene dispenser placed in a chamber of water subjected to an incoming flow of cooler water, the water will constrict at a rate approximately ten times faster than the polystyrene dispenser. Thus the internal pressure of the dispenser will be lower than the pressure exerted by the surrounding water. Consequently, water will be drawn into the dispenser through the opening where it may become saturated with the iodine. When the water flow to the reservoir is stopped and the water within the reservoir gradually returns to the higher resting or room temperature, the iodine-saturated water within the dispenser as well as the dispenser itself will gradually return to a resting temperature and will expand. Since the water expands at a rate faster than the dispenser, there will be a higher pressure within the dispenser than in the surrounding water. Consequently, some iodine-saturated water will be expelled through the opening of the dispenser and introduced into the surrounding water in the reservoir.

The system will similarly work, in the reverse order, when the temperature of the water supply fed to the treatment chamber is higher than the resting temperature for the treatment chamber, or when the coefficient of cubical expansion of the water is less than the coefficient of cubical expansion of the dispenser material.

To ensure saturation of the water contained within the dispenser with the agent before the water is ejected back into the surrounding supply, it is desirable to control the residence time (Rt) of the water within the dispenser.

The residence time is affected by the rate at which the dispenser and its contents expands or contracts. This in turn depends upon the coefficient of cubical expansion of the dispenser material and the coefficient of cubical expansion of the water. As well, the rate of expansion or contraction is affected by the rate at which the water is allowed to flow into or out of the dispenser. By adjusting the size of the dispenser opening, a slower or faster flow rate may be achieved. (Note that the dispenser opening will also expand and contract with changes in temperature.)

For larger containers, it may be advantageous to use a number of dispensers, and/or to use iodine of enhanced solubility.

The agent dispenser of this invention can also be housed in a treatment chamber that is connected to the main gas or liquid flow, and to the reservoir. For example, in the water reservoir/filter application, the treatment chamber would receive part of the new water fed to the reservoir, and its contents would be drawn to and through the reservoir when water is drawn from the reservoir.

The invention can be used in any situation where agents are to be added to gases or liquids and temperature differences can be brought to bear upon the dispenser as described. For example, it would also be used to impart vitamins or minerals to water, etc.

BRIEF DESCRIPTION OF THE DRAWINGS

The invention will now be described merely by way of illustration with reference to the accompanying drawings in which:

FIG. 1 is a sectional view through one embodiment of an apparatus in accordance with this invention;

FIG. 2 is an exploded perspective view, with certain items shown in phantom, of one embodiment of an agent dispenser in accordance with this invention;

FIG. 3 is an exploded sectional view through the agent dispenser shown in FIG. 2 when taken as indicated by the arrows 3—3 of that Figure;

FIG. 4 is an exploded sectional view through the agent dispenser shown in FIG. 2 when taken as indicated by the arrows 4—4 of that Figure;

FIG. 5 is a schematic view of an apparatus for treating a commercial water supply in accordance with this invention;

FIG. 6 is a sectional elevation of an apparatus for treating a domestic water supply in accordance with this invention;

FIG. 7 is a sectional elevation of a personally portable apparatus for treating a water supply in accordance with this invention; and FIG. 8 is a diagram of the stages of expansion and contraction that the agent dispenser as claimed by the invention undergoes.

DESCRIPTION OF A PREFERRED EMBODIMENT

The agent dispenser when used on its own, or when used with the apparatus or method as claimed in the present invention, has a broad range of uses for introducing agents into a liquid or gas. It may be utilized in situations where temperature changes exist or can be created in a gas or liquid to selectively drive the release of the agent from the dispenser into such gas or liquid.

One particular embodiment of the invention as claimed features an agent dispenser for adding iodine to water and an apparatus and method for such treatment. A primary example of the use of this dispenser and the method of use is the aforementioned water filtration system in which the filter rests in tepid water. In this environment, bacteria tend to settle on the filter and grow relatively actively. This can lead to contamination of the very water that is being filtered. By introducing iodine into the water in which the filter rests, the bacteria growth may be reduced and even stopped. The purpose of the method and apparatus described below is to ensure that iodine is introduced into the system each time filtered water is drawn off and unfiltered water is added. The iodine will be captured by the filter prior to the discharge of filtered water.

The apparatus 10 is depicted in FIG. 1 in the form of an in line water filter. The apparatus includes a reservoir 12 from which filtered water may be discharged through outlet means 16 at its upper end. At the lower end of the reservoir 12 a treatment chamber 18 is located. Water may be introduced into the treatment chamber 18 through inlet means 14. Above the treatment chamber 18, the reservoir is provided with a filter element 20 containing a suitable filter material such as granular activated carbon indicated at 22.

Agent Dispenser

Figure 2:
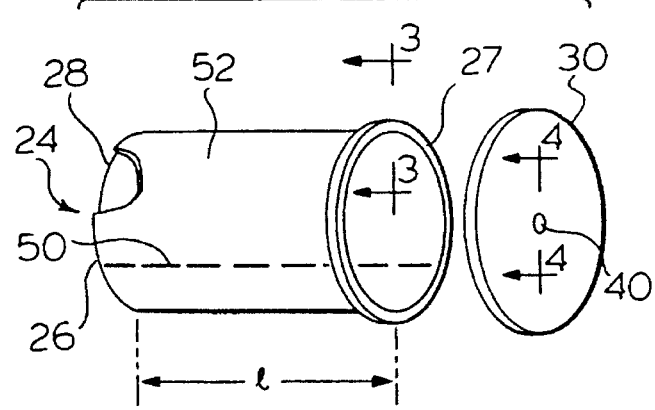
Figure 4:
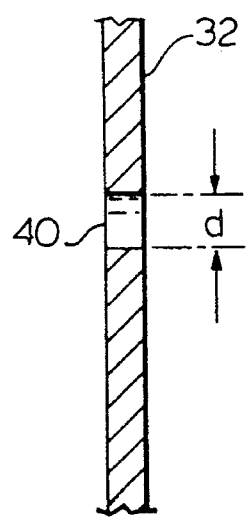
Figure 3:
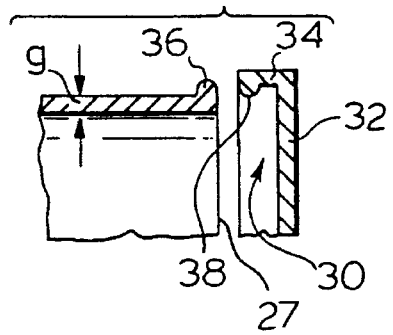

Within the treatment chamber 18, there is disposed an agent dispenser generally indicated at 24 and shown in greater detail in FIGS. 2–4. The dispenser 24 is constructed of a material having a coefficient of cubical expansion that differs from the coefficient of cubical expansion of the water. The coefficient of cubical expansion may be defined as the increment of volume of a unit volume for a rise of temperature of one degree. In the present example, it is preferred that there be a significant difference in the coefficients; preferably by a magnitude of ten. The coefficient of cubical expansion of crystalline polystyrene is approximately one-tenth of the coefficient, of cubical expansion of water. Consequently, it has been found that a dispenser constructed of crystalline polystyrene is suitable for use when the liquid is water. The coefficient of cubical expansion of glass differs from that of water by even a greater amount, however a glass dispenser may be hazardous when used with a consumable water supply. The dispenser 24 may be constructed in any shape that is desired. In the present example, a cylindrically shaped dispenser is illustrated. The dispenser 24 as shown in FIG. 2 has first and second open ends 26 and 27. These may be closed by fastening means as described below. Integrally formed with the first open end is a circular first end member indicated at 28. The second open end 27 of the dispenser 24 is closed by a second end member defining a closure generally indicated at 30. The closure 30 comprises a generally circular portion 32 which is integrally formed with a resilient peripheral skirt 34.

The closure 30 may be removably attached in different ways to the second open end 27 of the dispenser 24. In the embodiment shown in FIGS. 2 and 3, the dispenser 24 adjacent the second open end 27 is formed with an outwardly projecting annular lip 36 while a cooperating inwardly projecting annular lip 38 is provided on the peripheral skirt 34 of the closure 30. To permit removal of the closure 30 and its replacement on the dispenser 24, the peripheral skirt 34 should be sufficiently flexible to allow the lip 38 to snap over the lip 36. In this way, when the agent within the dispenser is exhausted, the closure may simply be removed and a fresh supply of the agent placed therein, after which the closure may be closed once more. A threaded closure and cooperating threaded dispenser adjacent the second open end may alternatively be used to permit the removal and replacement of the closure 30 on the dispenser 24.

The closure 30 may alternatively be sealed to prevent misuse. Such dispensers would be replaceable, as sealed units, when exhausted.

Generally at its centre the closure cap 30 is provided with a generally circular opening 40 (FIG. 4). The size of the opening 40 directly affects the rate of flow of water into and out of the dispenser. Consequently, in cases where the agent requires a longer time to evaporate or dissolve into the liquid or gas contained within the dispenser, it may be necessary to make the opening 40 smaller. This will ensure that most of the liquid or gas remains within the dispenser for an extended time, and thus become saturated with the agent. On the other hand, in cases where the agent evaporates or dissolves quickly into the liquid or gas, it may be desirable to make the opening 40 larger, or provide more than one opening on the dispenser 24. This will permit the treated liquid or gas to be resident in the treatment chamber for a shorter period of time.

Figure 6:
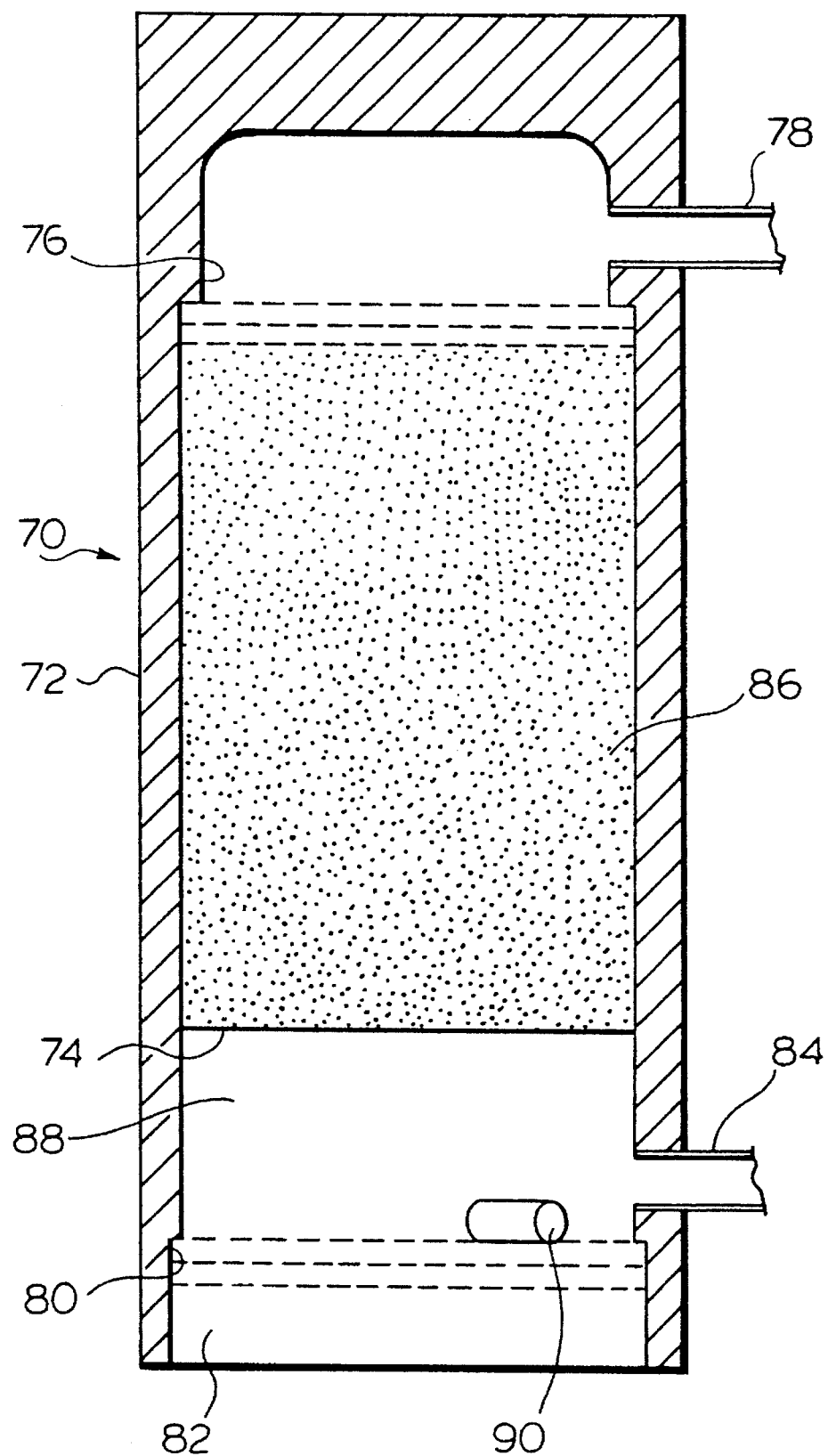

It will be seen from FIGS. 1 or 6 that the dispenser 24 can be disposed horizontally within the treatment chamber 18 so that it is resting with its outer wall supported on the base wall of the treatment chamber generally adjacent to the inlet means.

A miscible agent indicated at 50 in FIG. 2 is placed within the dispenser and the closure 30 is repositioned thereon. The agent may be in any desired form, as long as it is capable of mixing with the liquid or gas that is being treated. If desired, other materials such as carriers and materials which affect the miscibility of the agent in the liquid or gas can be admixed with the agent. Presently, the use of the dispenser 24 for treating water with iodine is being considered. For this particular application an agent consisting of solid iodine crystals is suitable.

Generally, the dispenser 24 will be initially charged with iodine crystals in such an amount that the crystals are disposed entirely below the opening 40, when the dispenser is lying on its side.

The dispenser 24, when submersed in the liquid or gas present in the treatment chamber 18, will fill with some of the liquid or gas. Thus, when treating water with iodine, the dispenser 24 containing iodine crystals will also become filled with water. The water contained within the dispenser will eventually become saturated with dissolved iodine. The iodine-saturated water contained within the dispenser 24 is referred to hereafter as treated contents 52.

Method for Treating Water with Iodine

Figure 8A:
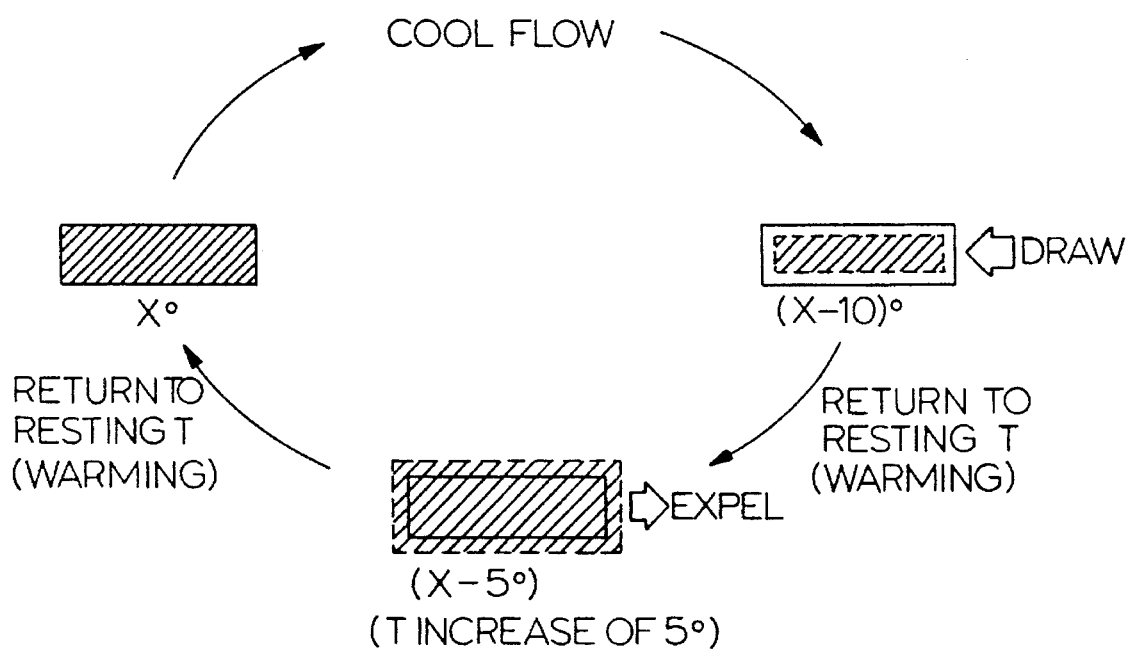
Figure 8B:
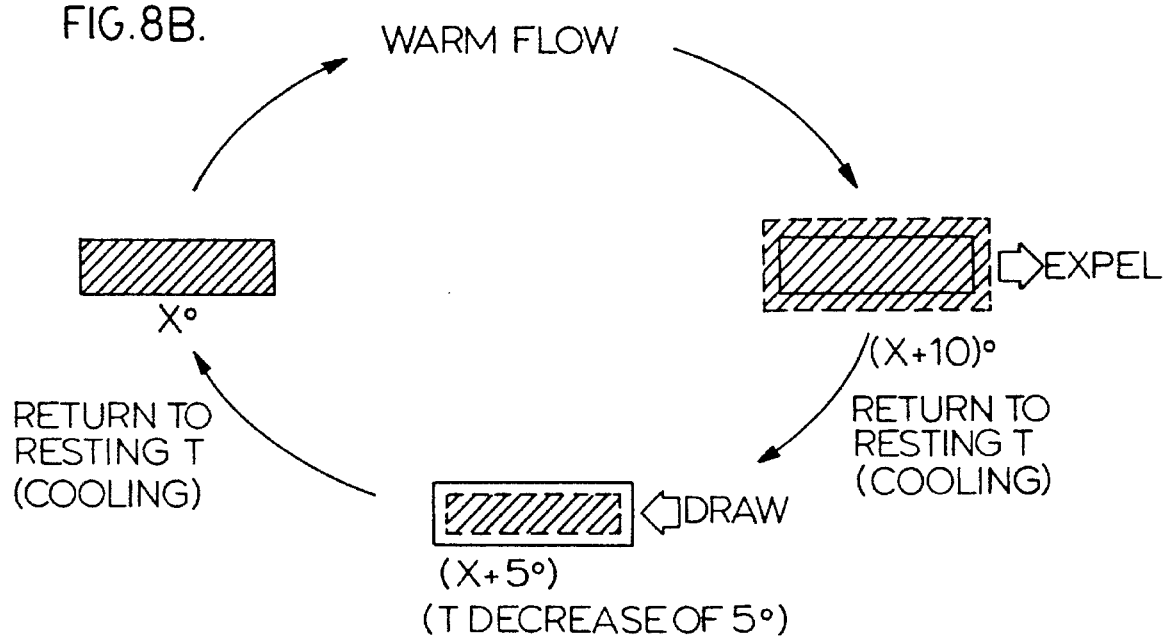

Considering the situation when no new water has flowed through the inlet means 14 for some time, the dispenser 24, and its treated contents 52, will be in thermal equilibrium with the water in the treatment chamber 18. In other words, the dispenser 24 and treated contents 52 will be at the same resting temperature as the water surrounding the dispenser. This situation is shown in FIG. 8.

If a valve or faucet (not shown) is now operated (FIG. 8) to permit the flow of water through the inlet means 14, and assuming such incoming water is at a lower temperature than the resting temperature of the water in the treatment chamber, as is usually the case, then the dispenser 24 will immediately be surrounded by cooler water and will no longer be in thermal equilibrium therewith.

Heat will flow from the dispenser 24, and from its treated contents 52, to the cooler surrounding water causing the temperature of the dispenser 24 and its treated contents 52 to fall. As the temperature falls, the treated contents 52 of the dispenser 24 will contract. (In fact, the dispenser itself will contract as it cools, however, in the case of a crystalline polystyrene dispenser, the rate of contraction is negligible compared to the rate of contraction of the treated contents.) The contraction of the treated contents 52 will cause an induction of water from the treatment chamber 18 through the opening 40 into the dispenser 24 (FIG. 8). The additional water drawn into the dispenser 24 will soon become saturated with dissolved iodine.

When the valve or faucet is disengaged and the water stops flowing through the inlet means 14, the water in the treatment chamber 18 as well as the dispenser 24 and its treated contents, will gradually return to the resting temperature. In the present example, the treated contents 52 would gradually increase in temperature until they reach the resting temperature and are once again in thermal equilibrium. As the treated contents 52 of the dispenser 24 return to the resting temperature, they will expand. (Again, the crystalline polystyrene dispenser 24 itself will also expand, but at a much lower, almost negligible rate). Consequently, some of the treated contents 52 will be expelled from the dispenser 24 into the treatment chamber 18 (FIG. 8). Through the process of diffusion, the expelled iodine-saturated water will mix with the remainder of the water contained within the treatment chamber 18, including the fresh, untreated water recently added to the system.

In this way each new supply of water to the treatment chamber 18 may become treated with iodine, and each treated supply of water may flow to the reservoir 12.

It should be understood that the process will work, in the reverse order, when the temperature of the water supply through the inlet means is warmer than the resting temperature in the treatment chamber. This is depicted in the lower portion of FIG. 8. Also, the process will work in the reverse order when the coefficient of cubical expansion of the liquid or gas is less than the coefficient of cubical expansion of the dispenser material.

The amount of iodine ultimately introduced into the surrounding water in the reservoir 12 will depend upon the volume of the dispenser 24, the temperature range between the resting temperature and the temperature of the incoming supply, the coefficient of cubical expansion of the material from which the dispenser 24 is constructed and to some extent the size of the dispenser opening 40.

Figure 5:
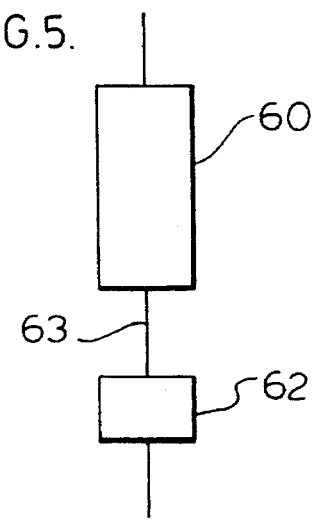

In the apparatus as depicted in FIG. 1, the treatment chamber 18 and the reservoir 12 constitute a single vessel and merely occupy regions therein. It may be appreciated that, for larger water supplies such as may exist in commercial buildings and the like, it may be desirable to provide the two components separately. This is illustrated schematically in FIG. 5, wherein the reservoir and filter element are illustrated at 60 and the treatment chamber is illustrated at 62. Flow means 63 are provided to permit the flow of treated water from the treatment chamber 62 to the reservoir 60. One advantage in separating the treatment chamber 62 from the reservoir 60 is the increased efficiency given to the agent dispenser. The treatment chamber 62 would have a much smaller volume than the reservoir 60. Consequently, when cold (or hot) water is added to the chamber 62, the overall temperature in the chamber will drop (or rise) faster and to a greater extent than it would if the chamber was incorporated in the much larger volume reservoir 60. Such an arrangement has proven effective in treating a reservoir 60 holding approximately 280,000 gallons (approximately 1,260,000 liters) of water with a small treatment chamber 62 containing a cylindrical dispenser having a length of 3 feet (approximately 0.93 meters), radius of 1 foot (approximately 0.31 meters) and an opening of 0.25 inches (approximately 64 millimeters).

A further embodiment of the invention for water filter treatment may be in the form of a domestic countertop device for use in a kitchen, bathroom, or office. In this case, it is assumed that the location will have a conventional domestic faucet. It is also assumed that such faucet will be generally surrounded by a countertop, or other form of stand or work surface. The device, shown in FIG. 6, is intended to be a portable free-standing device that is located beside the faucet. The device is generally indicated at 70 in FIG. 6. It has a side wall 72 defining a reservoir 74. At its upper end, a thickened side wall portion 76 is provided, and a spout 78 is secured in the side wall portion 76. The spout 78 is located at a convenient height for filling a jug or kettle placed on the countertop below it. At its lower end, the side wall 72 defines a threaded portion 80, receiving a threaded end closure 82. An inlet hose 84 is connected to the side wall 72, and may be adapted by any suitable means known in the art to connect to the faucet (not shown). The side wall 72 is adapted to receive a filter element indicated generally at 86, the filter 86 terminating short of the end closure 82. The filter element contains a suitable filter material such as granular activated carbon. Between the end closure 82 and the filter element 86, a space is left providing a treatment chamber 88. An agent dispenser 90 is received in the treatment chamber 88 adjacent to the inlet hose 84. An agent consisting of solid iodine crystals is suitable for this application. The removable end closure 82 permits the removal of the agent dispenser 90 and the filter element 86 from time to time for replenishment or renewal if desired. It has been found that a dispenser 90 having a generally cylindrical shape, with a length of 3 inches (approximately 762 millimeters), a radius of 1.25 inches (approximately 318 millimeters) and an opening of 0.125 inches (approximately 32 millimeters) is suitable for treating a reservoir of 4 gallons (approximately 18 liters) containing a filter element.

In this way, the countertop unit provides a self-contained portable water filter incorporating its own treatment chamber and agent dispenser. It may be stored on the kitchen countertop and used from time to time when it is desired to draw off a jug of clean drinking water. The filter element removes impurities existing in the water while the agent dispenser introduces a quantity of iodine into the water to prevent the growth of bacteria on the filter.

The invention may also be embodied in a personally portable device for use by travellers, office workers and the like who may have reason to be concerned about the quality of the water they may be drinking as they move from place to place. An example of such a device is shown in FIG. 7. In this example, the invention preferably comprises a compact, generally rectangular case 100, defining three generally cylindrical parallel spaced apart reservoirs 102, 104 and 106. Reservoirs 102 and 104 are connected at the first junction 108, and reservoirs 104 and 106 are connected at the second junction 110. In this way, the three chambers are essentially connected end-to-end, in a compact, easily portable configuration. Filter elements 112, 114 and 116 are located in respective reservoirs 102, 104, and 106. The filter elements contain a suitable filter material such as granular activated carbon. Screens 117 are placed at the ends of each filter element to hold the filter material in place.

Space is provided adjacent the reservoir 102 for a treatment chamber 103. An inlet means 118 connects to the end of the chamber 103, remote from junction 108. The inlet means 118 may be provided with a bulb 120 or other form of manual pumping device.

An outlet means 122 is connected to the end of reservoir 106 remote from second junction 110.

An agent dispenser 124 is located in the treatment chamber 103 adjacent the inlet means 118. An agent consisting of solid iodine crystals is suitable for this application. For convenience, securement clips 126 may be provided for securing hoses on either side of the case 100.

Using this configuration, the device may be small enough to fit easily in hand luggage, and yet provide an extended filter path that is treated with iodine saturated water. It is intended that such a device be disposable after a reasonable working life.

The iodine treatment method and apparatus described above is but one conceivable application for the invention. Many other uses are contemplated including agricultural applications involving the introduction of vitamins, minerals and other nutrients to both livestock and crop water supplies. In such applications, the agent dispenser may be placed into the gas or liquid being treated. For example, an agent dispenser containing vitamin and mineral agents may be placed within a livestock water trough. Every time the trough is refilled a quantity of the agent will be ejected into the potable water supply.

It is to be understood that what has been described are preferred embodiments of the invention. The invention nonetheless is susceptible to certain changes and alternative embodiments fully comprehended by the spirit of the invention as described above and the scope of the claims set out below.

The embodiments of the invention in which an exclusive property or privilege is claimed are defined as follows:

1. An apparatus for introducing an agent into a liquid or gas at a controlled rate, where the agent is miscible with such liquid or gas, said apparatus comprising:

(a) a reservoir for storing said liquid or gas, said reservoir being divided into a plurality of small units connected in series;

(b) an inlet means for supplying said liquid or gas to said reservoir;

(c) an outlet means for discharging said liquid or gas from said reservoir, said inlet means and said outlet means being located at opposite ends of each of said units of said series;

(d) a filter element containing granular activated carbon located in each unit of said reservoir adjacent to said outlet means; and (e) at least one agent dispenser located within said reservoir adjacent to said inlet means and surrounded by said liquid or gas, said dispenser containing said agent, and said dispenser being constructed of a hollow casing of polystyrene having a co-efficient of cubical expansion that differs from the co-efficient of cubical expansion of said liquid or gas, said dispenser having at least one opening for permitting the flow of said liquid or gas between said hollow casing and said reservoir;

wherein said agent is introduced into said liquid or gas surrounding said agent dispenser through said liquid or gas being drawn into and expelled from said dispenser through said at least one opening due to variations in the internal pressure of said dispenser resulting from thermal expansion and contraction of the dispenser and its contents due to variations in the temperature of said liquid or gas surrounding said dispenser.

2. An apparatus as claimed in claim 1 wherein said agent is at least one vitamin or mineral and said liquid or gas is a liquid.

3. An apparatus as claimed in claim 1 wherein said agent is iodine and said liquid or gas is water.

4. An apparatus as claimed in claim 1 wherein said hollow casing comprises:

(a) a generally cylindrical body having first and second open ends;

(b) a first and second end member for closing said first and second open ends; and (c) fastening means for fastening said first and second end members to said first and second open ends.

* * * * *